United States Patent [19]

Irving

[11] Patent Number: 4,537,725
[45] Date of Patent: Aug. 27, 1985

[54] DIARYLIODOSYL SALTS

[75] Inventor: Edward Irving, Burwell, England

[73] Assignee: Ciba-Geigy Corporation, Ardsley, N.Y.

[21] Appl. No.: 530,801

[22] Filed: Sep. 9, 1983

[30] Foreign Application Priority Data

Sep. 18, 1982 [GB] United Kingdom ............ 8226706
Jun. 10, 1983 [GB] United Kingdom ............ 8315925

[51] Int. Cl.$^3$ ............ C07F 15/02; C07F 7/22; C07F 9/68; C07F 9/92
[52] U.S. Cl. .................. 556/138; 568/8; 568/13; 568/16; 568/17; 556/64; 556/81; 556/76
[58] Field of Search .............. 568/8, 13, 17, 16; 260/440, 446, 447, 429.7, 439 R

[56] References Cited

U.S. PATENT DOCUMENTS

| | | |
|---|---|---|
| 3,981,897 | 9/1976 | Crivello ............... 260/440 |
| 4,136,102 | 1/1979 | Crivello ............... 260/440 |
| 4,151,175 | 4/1979 | Crivello et al. ........ 260/440 X |
| 4,219,654 | 8/1980 | Crivello .............. 260/439 R X |
| 4,238,394 | 12/1980 | Crivello et al. ....... 260/440 X |
| 4,310,469 | 1/1982 | Crivello ............... 260/440 X |
| 4,329,300 | 5/1982 | Crivello et al. ....... 260/446 X |
| 4,399,071 | 8/1983 | Crivello et al. ....... 260/446 |
| 4,450,360 | 5/1984 | Crivello et al. ....... 260/440 |

FOREIGN PATENT DOCUMENTS 1491540 11/1977 United Kingdom .
1516352 7/1978 United Kingdom .
1539192 1/1979 United Kingdom .

OTHER PUBLICATIONS

Chemical Abstracts, 93, 185332w, (1980).
Chemical Abstracts, 94, 3808w, (1981).
Chemical Abstracts, 77, 100956z, (1972).
F. M. Beringer et al., J. Org. Chem., 33, 2981, (1968).
J. G. Sharefkin et al., Org. Syn., 43, 665, (1963).

Primary Examiner—Helen M. S. Sneed
Attorney, Agent, or Firm—Luther A. R. Hall

[57] ABSTRACT

New diaryliodosyl salts have the formula

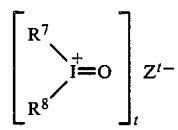

IV where
R$^7$ and R$^8$, which may be the same or different, each represent a monovalent aromatic radical of from 6 to 22 carbon atoms,
$Z^{t-}$ denotes a t-valent anion of formula $MX_n^-$ or $R^9SO_3^-$ or a t-valent anion of a halogen-free inorganic oxy acid,
t is 1, 2 or 3,
M represents an atom of a metal or metalloid,
X denotes a halogen atom, preferably of fluorine or chlorine,
n is 4, 5, or 6 and is one more than the valency of M, with the proviso that $MX_n^-$ can represent $SbOHF_5^-$, and
R$^9$ denotes a monovalent aliphatic or aromatic group of 1 to 20 carbon atoms.

These salts have utility as photocuring catalysts for cationically polymerizable materials such as epoxide resins and phenolic resins.

18 Claims, No Drawings

DIARYLIODOSYL SALTS

This invention relates to new diaryliodosyl salts having utility as catalysts for the polymerisation of cationically polymerisable materials and to their preparation.

It is well known that certain iodonium salts liberate an acidic species when subjected to actinic radiation and that this liberated acid may be used to polymerise or cure cationically polymerisable materials, such as epoxide resins, phenoplasts, and aminoplasts.

For example, British Patent Specification No. 1 491 540 describes aromatic iodonium complex salts having the general formula

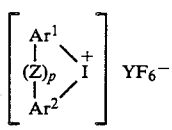   I where
- $Ar^1$ and $Ar^2$ may be the same or different and each represent an aromatic group having 4 to 20 carbon atoms which is an optionally substituted phenyl, thienyl, furanyl, or pyrazolyl group,
- Z represents an oxygen atom, a sulphur atom, or a group of formula $>S=O$; $>C=O$; $>SO_2$; $>N-R$ (in which R is a hydrogen atom, an alkyl group having 1 to 4 carbon atoms, or a carboxylic acid acyl group), a direct carbon-carbon bond, or a group of formula

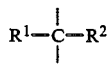

(in which $R^1$ and $R^2$ may be the same or different and each represent a hydrogen atom, an alkyl group having 1 to 4 carbon atoms, or an alkenyl group having 2 to 4 carbon atoms),
- p is zero or 1, and
- Y represents an atom of phosphorus, arsenic, or antimony.

British Patent Specification No. 1 516 352 describes salts having the formula

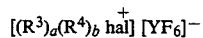   II where
- Y has the meaning assigned above,
- $R^3$ is a monovalent aromatic organic radical,
- $R^4$ is a divalent aromatic organic radical,
- "hal" is a halogen radical, and
- a is zero and b is 1, or a is 2 and b is zero.

British Patent Specification No. 1 539 192 discloses photopolymerisable compositions comprising at least one acid-polymerisable or acid-curable material and, as photosensitiser, at least one iodonium salt of formula

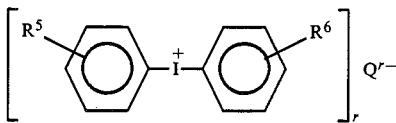   III where
- r is 1 or 2,
- $R^5$ and $R^6$, which may be the same or different, each represent a hydrogen or halogen atom, a nitro group, a hydrocarbon or substituted hydrocarbon group, or a heterocyclic group, and
- $Q^{r-}$ is an anion derived from an acid which is capable of polymerising or curing the acid-polymerisable or acid-curable material.

In an article by F. M. Beringer and P. Bodlaender, J. Org. Chem., 1968, 33, 2981-4, various diaryliodosyl salts, and their preparation, are described. The salts isolated were all acetates, trifluoroacetates, iodates, chlorides, bromides, or fluorides. An iodoxybenzene is self-condensed in the presence of hydroxide ions to give a diphenyliodosyl hydroxide which is neutralised with acetic, iodic, or trifluoroacetic acid. The other salts were made from these by materials. Typical amongst such salts are diphenyliodosyl acetate, trifluoroacetate, fluoride, chloride, bromide, and di(4-methylphenyl)iodosyl iodate. This article gives no indication of the behaviour of such salts when subjected to actinic radiation, and does not indicate any utility for them.

Surprisingly, it has now been found that certain novel iodosyl salts have utility as photo-activated curing or polymerising agents for cationically polymerisable materials; the prior art gives no indication that iodosyl salts would have this activity.

Accordingly, this invention provides novel diaryliodosyl salts of the general formula

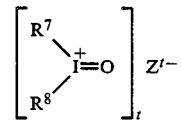   IV where
- $R^7$ and $R^8$, which may be the same or different, each represent a monovalent aromatic radical of from 6 to 22 carbon atoms,
- $Z^{t-}$ denotes a t-valent anion of formula $MX_n^-$ or $R^9SO_3^-$ or a t-valent anion of a halogen-free inorganic oxy acid,
- t is 1, 2 or 3,
- M represents an atom of a metal or metalloid,
- X denotes a halogen atom, preferably of fluorine or chlorine,
- n is 4, 5 or 6 and is one more than the valency of M, with the proviso that, when M represents antimony, n is 6, and five of the symbols X each represent a fluorine atom, then the sixth X represents a fluorine atom or a hydroxo group, and
- $R^9$ denotes a monovalent aliphatic or aromatic group of 1 to 20 carbon atoms.

Preferably M denotes an atom of antimony, bismuth, tin, or, more especially, of boron, iron, arsenic, or phosphorus. The anion $MX_n^-$ preferably, therefore, denotes a pentafluorohydroxoantimonate, hexachloroantimonate, hexafluoroantimonate or, more especially, a tetrafluoroborate, tetrachloroferrate, hexafluoroarsenate or hexafluorophosphate anion.

R⁹ preferably denotes an aromatic group of 6 to 12 carbon atoms, optionally substituted by one or more alkyl groups of 1 to 4 carbon atoms or by one or more halogen atoms, especially a phenyl or toluyl group, or an optionally halogen-substituted aliphatic group of 1 to 4 carbon atoms, especially a methyl or trifluoromethyl group.

Preferred halogen-free inorganic oxy acid anions are phosphate, including orthophosphate and hydrogen phosphates, sulphate and hydrogen sulphate anions.

It is further preferred that the groups $R^7$ and $R^8$ are the same, and are phenyl or naphthyl groups which may be unsubstituted or substituted by one or two groups selected from alkoxy groups of 1 to 4 carbon atoms, phenyl groups, and, especially, alkyl groups of 1 to 4 carbon atoms, nitro groups, and halogen atoms.

The diaryliodosyl salts of formula IV may be prepared by reaction of a diaryliodosyl hydroxide of formula

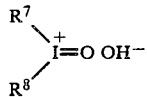   V where $R^7$ and $R^8$ are as hereinbefore defined, with an acid of formula $H_tZ$ (where such acids exist), this being the acid from which $Z^{t-}$ is derived, or with an alkali metal or ammonium salt of such an acid, $Z^{t-}$ being as hereinbefoe defined. This reaction is preferably effected in water or an aqueous organic solvent, at or below room temperature, preferably at 0° to 20° C.

In a variation of this procedure the hydroxide of formula V may be replaced by the corresponding carbonate of formula

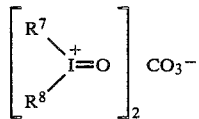   VI but in this process the acid of formula $H_tZ$ is used.

Salts of formula IV may alternatively be prepared by reaction of a diaryliodosyl acetate of formula VII, a trifluoroacetate of formula VIII, or a diaryliodosyl halide of formula IX

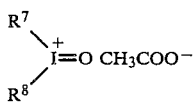   VII

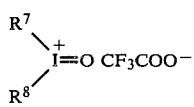   VIII

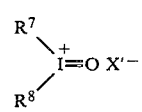   IX with an anion of formula $Z^{t-}$ where $R^7$, $R^8$, $Z^-$ and t are as hereinbefore defined and X' denotes a halogen atom. This reaction is preferably effected using an ammonium or alkali metal salt of the anion, especially the sodium or potassium salt, or in some instances the silver salt, in water or an aqueous organic solvent at room temperature or with gentle heating up to about 100° C.

If such a double decomposition is carried out with an aqueous solution of an alkali metal hexafluoroantimonate then, due to hydrolysis, the salt of formula V obtained is the pentafluorohydroxoantimonate: to obtain the corresponding hexafluoroantimonate it is necessary to add the alkali metal hexafluoroantimonate as a solid.

Diaryliodosyl compounds of formulae V to IX, used as starting materials in the above-described processes, are conveniently prepared by the method described by F. M. Beringer and P. Bodlaender, loc. cit., from iodoxyarenes, which can be prepared according to the method described by J. G. Sharefkin and H. Saltzman, Org. Syn., 1963, 43, 665–7, to which reference is made by Beringer and Bodlaender. One or two iodoxyarenes of formula X and XI $R^7IO_2$   X $R^8IO_2$   XI where $R^7$ and $R^8$ are as hereinbefore defined, are treated with an alkali metal hydroxide to form the diaryliodosyl hydroxide of formula V. Treatment of this with carbon dioxide gives the carbonate of formula VI, and treatment with acetic acid, trifluoroacetic acid, or a hydrohalic acid gives the acetate of formula VII, the trifluoroacetate of formula VIII, or the halide of formula IX.

As indicated above, the salts of this invention are useful as photoinitiators for the polymerisation of cationically polymerisable materials. Compositions comprising a diaryliodosyl salt of formula IV and a cationically polymerisable material are normally sensitive to radiation having a wavelength in the region of 200 to 600 nm, i.e., throughout the visible and ultraviolet spectral regions. Exposure for a relatively short period, particularly in the ultraviolet region, gives a polymer having desirable properties, Specific examples of diaryliodosyl salts of the present invention include:
bis(4-methoxyphenyl)iodosyl hexafluorophosphate
bis(4-fluorophenyl)iodosyl hexafluorophosphate
diphenyliodosyl hexafluorophosphate
bis(4-methylphenyl)iodosyl hexafluorophosphate
bis(4-biphenyl)iodosyl hexafluorophosphate
bis(2,4-dichlorophenyl)iodosyl hexafluorophosphate
bis(1-naphthyl)iodosyl hexafluorophosphate
bis(4-isopropylphenyl)iodosyl hexafluorophosphate
bis(3-nitrophenyl)iodosyl hexafluorophosphate
the corresponding tetrafluoroborates, hexafluoroarsenates, hexachloroantimonates, and hexafluoroantimonates, diphenyliodosyl 4-toluenesulphonate, diphenyliodosyl tetrachloroferrate, diphenyliodosyl orthophosphate and diphenyliodosyl sulphate.

The invention is illustrated by the following Examples.

Iodoxyarenes used in the Examples are prepared according to the method described by J. G. Sharefkin and H. Saltzman, loc. cit.

EXAMPLE 1

Diphenyliodosyl acetate monohydrate (1.87 g; prepared as described by F. M. Beringer and P. Bodlaender, loc. cit.), is dissolved in boiling water (25 ml) and the solution is treated with decolourising charcoal and filtered hot. A saturated aqueous solution of potassium hexafluorophosphate is added slowly to the filtrate until no further precipitation occurs. The mixture is then cooled and filtered. The residue is dried over phosphorus pentoxide in vacuo at room temperature to give diphenyliodosyl hexafluorophosphate (0.87 g), m.pt. 120°-130° C. (decomp.).

EXAMPLE 2

Iodoxybenzene (3.37 g) is added to a stirred 1N solution of sodium hydroxide at 0° C. After 2 hours the mixture is filtered and a solution of potassium hexafluorophosphate (1.32 g) in water (5 ml) is added. A flocculent precipitate forms immediately. This is filtered off, washed with ice-cold water, and dried over phosphorus pentoxide. It is recrystallized from a mixture of chloroform and petroleum ether, boiling range 40°-60° C., to give diphenyliodosyl hexafluorophosphate (0.18 g), m.pt. 130° C. (decomp).

EXAMPLE 3

Diphenyliodosyl trifluoroacetate (4.1 g; prepared according to F. M. Beringer and P. Bodlaender, loc. cit.) is dissolved completely in boiling water by adding it in portions, then the solution is treated with charcoal and filtered hot. To the hot filtrate is added a saturated aqueous solution of 1.84 g of potassium hexafluorophosphate and the resultant clear solution is cooled. A white precipitate forms and is filtered off to give diphenyliodosyl hexafluorophosphate (2.72 g) m.pt. 135°-136° C. (decomp.). (Found: C, 33.30; H, 2.36; F, 26.04; I, 29.18; P, 7:13; $C_{12}H_{10}F_6IOP$ requires C, 32.60; H, 2.28; F, 25.79; I, 28.71; P, 7.01%).

Spectral analysis shows: Infra-red (KBr disc) $\nu_{max}$ at 3100, 3065, 1580, 1565, 1470, 1445, 1010, 995, 990, 840 (broad), 755, 745, 740, 685, and 650 cm$^{-1}$. Ultra-violet $\lambda_{max}^{CHCl_3}$ 227 nm. N.M.R. (deuterated acetone) $\delta$ at 8.50-8.20 (m) and 7.85-7.40 (m).

The above values are compatible with the assigning of the structure diphenyliodosyl hexafluorophosphate to the product.

EXAMPLE 4

Iodoxybenzene (35.4 g) is added to a 1N solution of sodium hydroxide (300 ml) which is stirred and cooled to 0° C. After 2 hours the precipitate is removed by filtration and the filtrate is treated with carbon dioxide until it becomes neutral.

A portion of this neutralised solution (100 ml) is stirred and fluoroboric acid (40%) is added slowly until evolution of carbon dioxide ceases; a further quantity of this acid (2 ml) is then added. The precipitate which forms is filtered off, washed with ice-cold water, and dried to give diphenyliodosyl tetrafluoroborate (2.4 g) m.pt. 110°-120° C. (with decomp.).

Infra-red spectral analysis (KBr disc) shows $\nu_{max}$ at 3080, 3050, 1465, 1445, 1060 (broad), 985, 740, and 680 cm$^{-1}$.

EXAMPLE 5

Bis(4-methylphenyl)iodosyl trifluoroacetate (1.16 g; prepared as described by F. M. Beringer and P. Bodlaender, loc. cit.) is dissolved in boiling water (90 ml), filtered, and a saturated aqueous solution of 0.49 g of potassium hexafluorophosphate is added. The white precipitate is filtered off and dried to give bis(4-methylphenyl)iodosyl hexafluorophosphate (0.68 g), m.pt. 125° C. (with decomp.).

EXAMPLE 6

4-iodoxytoluene (12.5 g) is added to a stirred 2N solution of sodium hydroxide (100 ml) cooled to 0° C. After two hours the precipitate is removed by filtration. A cooled 10% solution of hexafluorophosphoric acid is added to the filtrate at 0° C. with stirring. The white precipitate which forms is collected by filtration, washed with water, and dried in air to give bis(4-methylphenyl)iodosyl hexafluorophosphate (7.6 g) m.pt. 127°-128° C.

A sample submitted for spectral analysis gives the following results:

Infra-red (KBr disc) $\nu_{max.}$, at 1475, 1180, 995, 848, 801, 745. 'H n.m.r. (deuterated acetone) $\delta$ at 7.65 (8H, d of d) and 2.4 (6H, s).

U.V. $\lambda_{max}^{CHCl_3}$ 238 nm.

EXAMPLE 7

Bis(4-isopropylphenyl)iodosyl trifluoroacetate is prepared by a similar method to that described by F. M. Beringer and P. Boedlander, loc. cit.) using 4-isopropyliodoxybenzene (8.3 g) as starting material. The trifluoroacetate is dissolved in boiling water. Potassium hexafluorophosphate (2 molar excess) in water is added and the solution is allowed to cool. The crystals which form are collected by filtration and dried in air to afford bis(4-isopropylphenyl)iodosyl hexafluorophosphate (0.4 g) m.pt. 84° C. Spectroscopic analysis shows:

I.R. (KBr disc) $\nu$max 2970, 1655, 1480, 1410, 992, 848. 'H nmr (d$^6$ acetone) $\delta$ at 7.85$\delta$ (8H, d of d); 2.75$\delta$ (2H, m); 1.2$\delta$ (12H, d).

U.V. (EtOH) $\lambda$max. 237.

EXAMPLE 8

Bis(4-fluorophenyl)iodosyl hexafluorophosphate is prepared in an analogous manner to bis(4-methylphenyl)iodosyl hexafluorophosphate in Example 6. A yield of 0.5 g,m.pt. 126° C. (with decomposition), is obtained from 4-fluoroiodoxybenzene (10.2 g).

Infra-red and proton magnetic resonance spectroscopy of the compound gives the analysis:

Infra-red (KBr disc) $\nu$max. at 1580, 1480, 1242, 1165, 848, 730.

'H nmr (deuterated acetone) $\delta$ at 8.3 and 7.4 broad multiplets.

U.V. $\lambda$max. 225 nm, shoulder at 258 nm.

EXAMPLE 3

Diphenyliodosyl trifluoroacetate (1.2 g; prepared according to the method of F. M. Beringer and P. Boedlander, loc. cit.) is dissolved in hot water, treated with charcoal and filtered hot. An aqueous solution of potassium hexafluoroarsenate (0.7 g) is added to the filtrate and the resultant solution cooled. The white precipitate which forms is collected by filtration and dried in air to give diphenyliodosyl hexafluoroarsenate (0.64 g), m.pt. 135°-138° C. (decomposition). Spectral analysis shows:

I.R. (KBr disc) $\nu$max at 1470, 1445, 1200, 1133, 989, 738, 704.

'H nmr (deuterated acetone) $\delta$ at 8.2 m; and 7.65 m.

EXAMPLE 10

Iodoxybenzene (11.8 g) is added to a stirred 1 molar solution of sodium hydroxide at 0° C. After two hours the mixture is filtered and the filtrate is treated with carbon dioxide at 0° C. until it becomes neutral. An aqueous solution of 4-toluenesulphonic acid is added with vigorous stirring until complete liberation of carbon dioxide is achieved. The solid which forms is collected by filtration, washed with ice-cold water and dried in vacuo over phosphorus pentoxide to give diphenyliodosyl 4-toluenesulphonate (7.75 g), m.pt. 102° C. Spectral analysis shows:

Infra-red (KBr disc) $\nu$max. at 1470, 1442, 1200, 1120, 1032, 1010, 740, 685.

'H nmr (deuterated acetone) $\delta$ at 8.15 m; 7.5 m, 6.95 d, 14 protons in all, 2.25 s, 3H.

U.V. $\lambda_{max}^{H2O}$ 222 nm, shoulder at 262 nm.

EXAMPLE 11

Diphenyliodosyl trifluoroacetate (1 g) is dissolved in boiling water. The solution is treated with activated carbon, then filtered hot. A solution of ammonium tetrachloroferrate is added and a white precipitate forms. The solid is collected by filtration and dried in air to give diphenyliodosyl tetrachloroferrate (0.44 g), m.pt. 164° C.

EXAMPLE 12

Iodoxybenzene (11.8 g) is added to a stirred 1N solution of sodium hydroxide (100 ml) at 0° C. Stirring is continued for 1½ hours at this temperature. The mixture is then filtered to remove precipitated sodium iodate. The filtrate is treated with a 10% solution of orthophosphoric acid until it becomes acid (pH 5). Crystallisation is effected by cooling the solution to 0° C. overnight. The crystals are collected by filtration and air-dried to afford diphenyliodosyl orthophosphate (2.5 g), m.pt. 115°–116° C. (with decomposition).

EXAMPLE 13

Diphenyliodosyl sulphate is prepared in an analogous manner to diphenyliodosyl orthophosphate in Example 12, except that a 10% solution of sulphuric acid is used in place of orthophosphoric acid. A yellow precipitate forms on addition of the acid; this is filtered and the solid collected. The yellowish solid is diphenyliodosyl sulphate (2.0 g), m.pt. 126°–128° C. (with decomposition).

EXAMPLE 14

3-Nitroiodoxybenzene (11.25 g), m.pt. 206° C. (decomposition), prepared in 75% yield according to the method described by J. G. Sharefkin and H. Saltzman, loc. cit., is added to a stirred solution (80 ml) of 1 molar sodium hydroxide at 0° C. After 90 minutes the mixture is filtered to remove the precipitated sodium iodate. Hexafluorophosphoric acid solution (10%) is added to the filtrate. As the pH becomes lower the iodosyl salt precipitates out of solution. The addition of acid is terminated when the pH reaches about 5. The precipitate is collected by filtration and dried in air. This is bis(3-nitrophenyl)iodosyl hexafluorophosphate, (0.2 g), melting point 182° C. (with decomposition).

The following Examples illustrate the use of the salts of this invention as photocatalysts for the polymerisation of cationically polymerisable materials. The resins used in these Examples are as follows:

Resin I denotes the diglycidyl ether of 2,2-bis(4-hydroxyphenyl)propane.

Resin II denotes 3,4-epoxycyclohexylmethyl 3,4-epoxycyclohexanecarboxylate.

Resin III denotes a resol made from phenol and formaldehyde having a phenol:formaldehyde molar ratio of 1:1.14, a viscosity at 25° C. of 0.7 Pa s and a solids content of 76%, neutralised with 4-toluenesulphonic acid.

EXAMPLE 15

The resin (10 g) is mixed with diphenyliodosyl hexafluorophosphate (0.3 g) and acetone (0.15 ml) and spread onto tinplate as a coating 10 μm in thickness. The coating is irradiated using a 80 w/cm medium pressure mercury arc lamp at a distance of 20 cm. The resins used, the irradiation times, and the properties of the irradiated coatings, are given in the following Table:

TABLE 1

| Resin | Irradiation time (secs) | Irradiated coating |
|---|---|---|
| I | 1 | hard, tack-free |
| II | 1 | hard, tack-free |

EXAMPLE 16

Resin III (100 g) and diphenyliodosyl 4-toluenesulphonate (3 g) are mixed and coated onto tinplate to give a coating 6–8 μm thick. The coating is irradiated using an 80 w/cm medium pressure mercury arc lamp at a distance of 20 cm., giving a tack-free film after 8 seconds.

What is claimed is:

1. A diaryliodosyl salt of formula

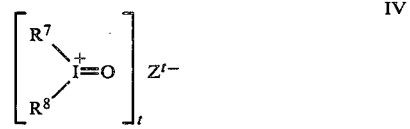

IV wherein $R^7$ and $R^8$, which are the same or different, represent phenyl, naphthyl or said phenyl or said naphthyl substituted by one or two groups selected from the group consisting of alkoxy of 1 to 4 carbon atoms, alkyl of 1 to 4 carbon atoms, phenyl, nitro and halogen, $Z^{t-}$ denotes a t-valent anion of formula $MX_n$— or $R^9SO_3$— or is a t-valent anion selected from the group consisting of phosphate, hydrogenphosphate, dihydrogenphosphate, sulfate and hydrogensulfate, t is 1, 2 or 3, M represents antimony, bismuth, tin, boron, iron, arsenic or phosphorus, X represents fluoro or chloro, n is 4, 5 or 6, and is one more than the valency of M, with the proviso that, when M represents antimony, n is 6 and five of X are each fluoro and the other X represents fluoro or hydroxo, and $R^9$ represents methyl, trifluoromethyl, phenyl or said phenyl substituted by alkyl of 1 to 4 carbon atoms or by halogen.

2. A salt as claimed in claim 1, in which $Z^{t-}$ denotes $MX_n^-$ where M represents an atom of boron, iron, arsenic, or phosphorus.

3. A salt as claimed in claim 1, in which $MX_n^-$ denotes a tetrafluoroborate, tetrachloroferrate, hexafluorophosphate, or hexafluoroarsenate anion.

4. A salt as claimed in claim 1, in which $Z^{t-}$ denotes $R^9SO_3^-$ where $R^9$ is an aromatic group of 6 to 12 carbon atoms or an aliphatic group of 1 to 4 carbon atoms.

5. A salt as claimed in claim 1, in which $Z^{t-}$ denotes a phosphate or sulfate anion.

6. A salt as claimed in claim 1, in which the groups $R^7$ and $R^8$ are the same.

7. A salt as claimed in claim 1, in which $R^7$ and $R^8$ represent a phenyl group which may be unsubstituted or substituted by one or two groups selected from the group consisting of alkyl groups of 1 to 4 carbon atoms, nitro groups, and halogen atoms.

8. Diphenyliodosyl hexafluorophosphate, diphenyliodosyl tetrafluoroborate, bis(4-methylphenyl)iodosyl hexafluorophosphate, bis(4-isopropylphenyl)iodosyl hexafluorophosphate, bis(4-fluorophenyl)iodosyl hexafluorophosphate, diphenyliodosyl hexafluoroarsenate, diphenyliodosyl 4-toluenesulfonate, diphenyliodosyl tetrachloroferrate, diphenyliodosyl orthophosphate, diphenyliodosyl sulfate, or bis(3-nitrophenyl)iodosyl hexafluorophosphate.

9. A process for the preparation of a diaryliodosyl salt as claimed in claim 1, which comprises reaction of a diaryliodosyl hydroxide of formula

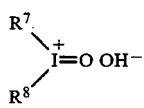

V with an acid which is of formula $HMX_n$ or $HR^9SO_3$ or is a halogen-free inorganic oxyacid, or with an alkali metal or ammonium salt of such an acid.

10. A process according to claim 9, which is effected in water or an aqueous organic solvent at or below room temperature.

11. A process as claimed in claim 10, which is effected at 0° C. to 20° C.

12. A process for the preparation of a diaryliodosyl salt as claimed in claim 1, which comprises reaction of a diaryliodosyl carbonate of formula

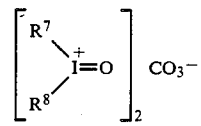

VI with an acid of formula $HMX_n$ or $HR^9SO_3$, or a halogen-free inorganic oxyacid.

13. A process as claimed in claim 12, which is effected in water or an aqueous organic solvent at or below room temperature.

14. A process according to claim 13, which is effected at 0° to 20° C.

15. A process for the preparation of a diaryliodosyl salt as claimed in claim 1, which comprises reaction of a diaryliodosyl acetate of formula

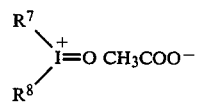

VII a diaryliodosyl trifluoroacetate of formula

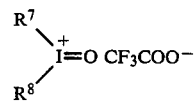

VIII or a diaryliodosyl halide of formula

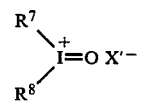

IX with an anion of formula $Z^{t-}$, where $X'$ denotes a halogen atom.

16. A process as claimed in claim 15, which is effected using an ammonium or alkali metal salt of the anion $Z^{t-}$.

17. A process as claimed in claim 15, which is effected in water or an aqueous organic solvent.

18. A process according to claim 17, which is effected at room temperature or with heating up to 100° C.

* * * * *